(12) United States Patent
Jawidzik

(10) Patent No.: US 10,925,680 B2
(45) Date of Patent: Feb. 23, 2021

(54) FOOT CONTROLLER WITH ADJUSTABLE TREADLE

(71) Applicant: Alcon Inc., Fribourg (CH)

(72) Inventor: Geoffrey C. Jawidzik, Mission Viejo, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 16/572,719

(22) Filed: Sep. 17, 2019

(65) Prior Publication Data

US 2020/0085515 A1 Mar. 19, 2020

Related U.S. Application Data

(60) Provisional application No. 62/732,705, filed on Sep. 18, 2018.

(51) Int. Cl.
| | | |
|---|---|---|
| *A61B 34/00* | (2016.01) | |
| *A61F 9/007* | (2006.01) | |
| *G05G 1/40* | (2008.04) | |
| *A61B 17/00* | (2006.01) | |

(52) U.S. Cl.
CPC .............. *A61B 34/25* (2016.02); *A61F 9/007* (2013.01); *G05G 1/40* (2013.01); *A61B 2017/00199* (2013.01); *A61B 2017/00977* (2013.01)

(58) Field of Classification Search
CPC ......................... G05G 1/40; A61B 2017/00977
See application file for complete search history.

(56) References Cited

U.S. PATENT DOCUMENTS

| | | | |
|---|---|---|---|
| 5,787,760 A | 8/1998 | Thorlakson | |
| 6,360,630 B2* | 3/2002 | Holtorf | G05G 1/30 200/86.5 |
| 6,862,951 B2 | 3/2005 | Peterson | |
| 6,962,581 B2 | 11/2005 | Thoe | |
| 7,019,234 B1 | 3/2006 | Mezhinsky | |
| 7,084,364 B2* | 8/2006 | Mezhinsky | H01H 3/14 200/310 |
| 7,185,555 B2 | 3/2007 | Peterson | |
| 7,193,169 B2 | 3/2007 | Mezhinsky | |
| 7,381,917 B2 | 6/2008 | Dacquay | |
| 7,619,171 B2 | 11/2009 | Horvath | |
| 7,626,132 B2 | 12/2009 | Mezhinsky | |
| 8,465,473 B2 | 6/2013 | Horvath | |
| 8,680,412 B2 | 3/2014 | Horvath | |
| 8,749,188 B2 | 6/2014 | Tran | |
| 9,240,110 B2* | 1/2016 | Roth | H01H 3/14 |
| 9,271,806 B2 | 3/2016 | Tran | |
| 9,439,806 B2 | 9/2016 | Eastman | |
| 9,597,497 B2 | 3/2017 | Swain | |
| 10,243,557 B2 | 3/2019 | Ekvall | |
| 2003/0047434 A1* | 3/2003 | Hanson | A61B 17/00 200/86.5 |
| 2004/0035242 A1 | 2/2004 | Peterson | |
| 2005/0039567 A1* | 2/2005 | Peterson | G05G 1/445 74/561 |
| 2006/0145540 A1 | 7/2006 | Mezhinsky | |

(Continued)

Primary Examiner — Vicky A Johnson

(57) ABSTRACT

The disclosed embodiments of the present technology relate to a foot controller with an adjustable treadle assembly including an adjustable treadle surface member slidably coupled to a fixed treadle plate and a latch assembly to adjust the adjustable treadle surface member to fixed positions relative to the treadle plate.

15 Claims, 10 Drawing Sheets

(56) References Cited

U.S. PATENT DOCUMENTS

| | | |
|---|---|---|
| 2006/0219049 A1* | 10/2006 | Horvath ................ H01H 21/26 74/560 |
| 2014/0135785 A1 | 5/2014 | Tran |
| 2014/0364864 A1 | 12/2014 | Lynn |
| 2015/0173725 A1 | 6/2015 | Maxson |
| 2018/0050671 A1 | 2/2018 | Yahagi |
| 2018/0132958 A1 | 5/2018 | Jochinsen |
| 2020/0064879 A1 | 2/2020 | Jawidzik |
| 2020/0085515 A1* | 3/2020 | Jawidzik ................ H01H 3/14 |

* cited by examiner

FOOT CONTROLLER WITH ADJUSTABLE TREADLE

BACKGROUND

Field of the Disclosure

The present disclosure relates to a foot controller and, more specifically, to a foot controller with an adjustable treadle.

Description of Related Art

Patient treatment apparatus or surgical systems, such as surgical equipment used when performing ophthalmic surgery, may require controlling a variety of subsystems, such as pneumatic and electronically driven subsystems, therapeutic lasers, etc.

The operation of the subsystems can be controlled by a microprocessor-driven console. The microprocessor controls within a surgical console receive mechanical inputs from either the operator of the surgical system or from an assistant to govern the operation of a subsystem within the patient treatment apparatus. Control input devices may include switches on the console, remote hand switches, remote foot controllers, and other control input devices.

Some procedures benefit from a treadle-driven foot controller which, like regulating speed with a pedal of an automobile, allows an operator to regulate a variable control input, e.g. cut speed of a vitrectomy probe. For these treadle-driven foot controllers, the mechanical inputs can originate from the movement of the foot of an operator which are translated into electrical signals that are fed to the microprocessor controls.

Foot controllers typically have a fixed size and sometimes include a heel cup which supports the operator's foot. However, an operator with a smaller foot can have trouble reaching the treadle pedal to drive the variable control input. Also, a single heel cup position can result in perceived or actual non-optimal placement of the foot relative to the buttons for some users.

SUMMARY

The disclosed embodiments of the present technology relate to a foot controller with an adjustable treadle assembly. The adjustable treadle assembly can include a treadle plate, an adjustable treadle surface member, and a latch assembly.

The foot controller can include a control assembly that determines the angular position of the treadle assembly and converts the angular position into a first signal describing the angular position of the treadle assembly. The foot controller is communicatively coupled with a surgical console, and wherein the first signal describing the angular position of the pedal surface is used to control a surgical tool coupled with the surgical console.

The treadle plate can be rotatably coupled with the base of the foot controller and can have a variable angular position with respect to the base. The treadle plate can have at least one channel in the surface of the treadle plate, at least one rail in the channel, and at least one shuttle slidably coupled to the at least one rail. In some cases, the treadle plate has two channels in the surface of the treadle plate each of the two channels includes one rail. The treadle plate further can also have two shuttles slidably coupled to each of the rails in the two channels. The adjustable treadle surface member can have a heel cup and can be coupled to the treadle plate via the at least one shuttle allowing the adjustable treadle surface member to move along the rails to adjust the heel cup relative to the distal end of the foot controller.

The foot controller can also include a latch assembly including a lever that extends underneath the treadle plate. The treadle plate can further include a plurality of notches on the bottom surface near the distal end of the treadle plate. The lever can have at least one protrusion that selectively engages with at least one of the plurality of notches on a bottom surface of the treadle plate to adjust the adjustable treadle surface member to fixed positions relative to the treadle plate. In some cases, the lever includes a plurality of protrusions that selectively engage with one of the plurality of notches on a bottom surface of the treadle plate The latch assembly can also include a latch axis pin that acts as a fulcrum to selectively engage the at least one protrusion with at least one of the plurality of notches on a bottom surface of the treadle plate. In addition, the latch assembly can include a latch spring that provides resistance to a movement of the lever about the fulcrum and a return force on the lever. In some cases, the adjustable treadle surface member further extends downward at the distal end to shield the latch assembly and latch assembly can include a latch button located in an opening of the shielded area.

BRIEF DESCRIPTION OF THE DRAWINGS

For a more complete understanding of the present technology, its features, and its advantages, reference is made to the following description, taken in conjunction with the accompanying drawings, in which.

DESCRIPTION

Figure 1:
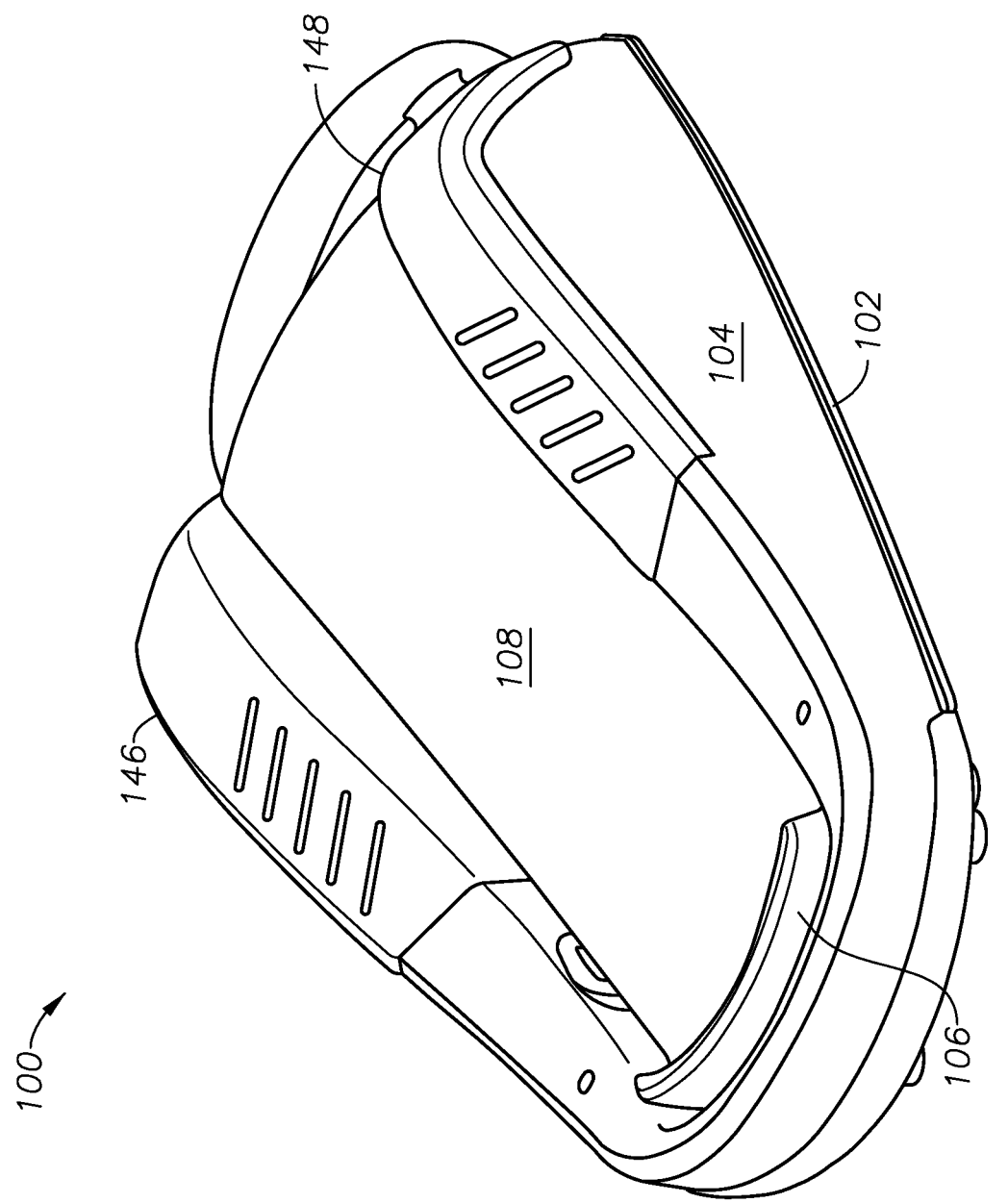
FIG. 1 illustrates a foot controller with an adjustable treadle according to some embodiments of the present technology.

FIG. 1 illustrates a foot controller 100 with a base 102, a frame 104, and a treadle 108. In some cases, the treadle 108 includes a heel cup 106 at a proximal end of the treadle 108. The treadle 108 is a foot-controlled assembly which can be oriented at a default angular position with respect to the base 102 and which can be rotationally depressed toward the base 102. The foot controller 100 can also include a control assembly (not shown) that can determine the angular position of the treadle 108 relative to the base and to convert the angular position into a signal. The foot controller 100 can be communicatively coupled with a console and the signal can be used to control the console, a console accessory, and/or another module used in conjunction with the console. For example, the foot controller 100 can be coupled with an ophthalmic surgical console and the signal from the control assembly can be used to control an ophthalmic surgical tool, e.g. a vitrectomy probe, a phacoemulsification hand piece, display settings, etc. The foot controller 100 can also include one or more buttons 146, 148 at a distal end of the frame 104. The buttons 146, 148 can, when pressed, generate additional signals for another control aspect of the console, console accessory, and/or another module used in conjunction with the console.

In some cases, the control assembly includes a position sensor (not shown). The position sensor can be rotationally coupled to the treadle 108 directly or through intermediate mechanical couplings such as gears. If gears are used, it is possible for the rotational motion to be mechanically amplified or attenuated according to the ratio of the number of teeth of the respective gears, as is well known. The position sensor may work through numerous possible well known mechanisms, for example, use of an optical encoder, or use of a potentiometer.

As explained above, there is a need in the art for a foot controller that can be adjusted to better accommodate operators' varying foot sizes. Therefore, the treadle 108 of the foot controller 100 can be a multi-part treadle assembly which allows for such an adjustment.

Figure 2A:
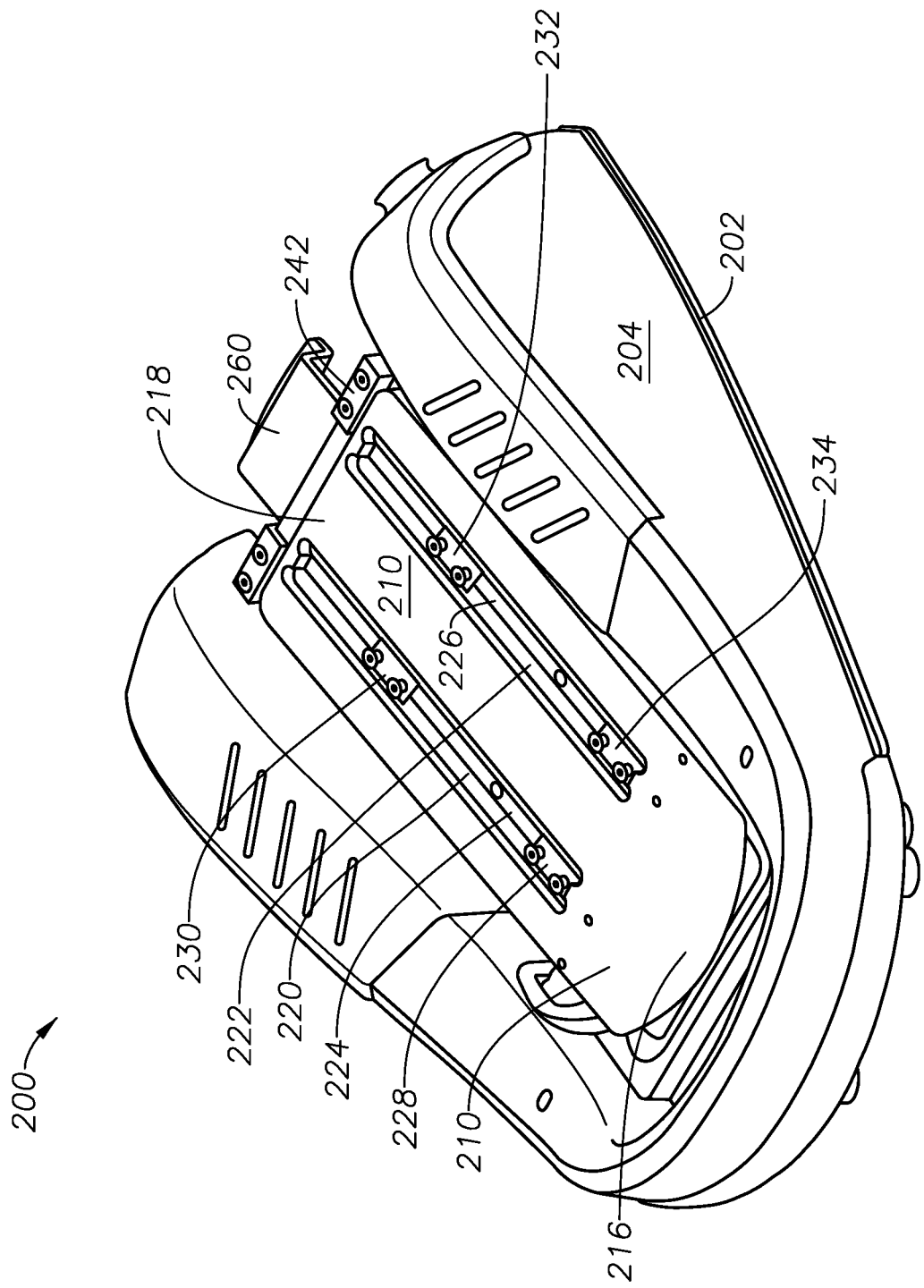
FIGS. 2A and 2B illustrate layered views of a treadle assembly of a foot controller.
Figure 2B:
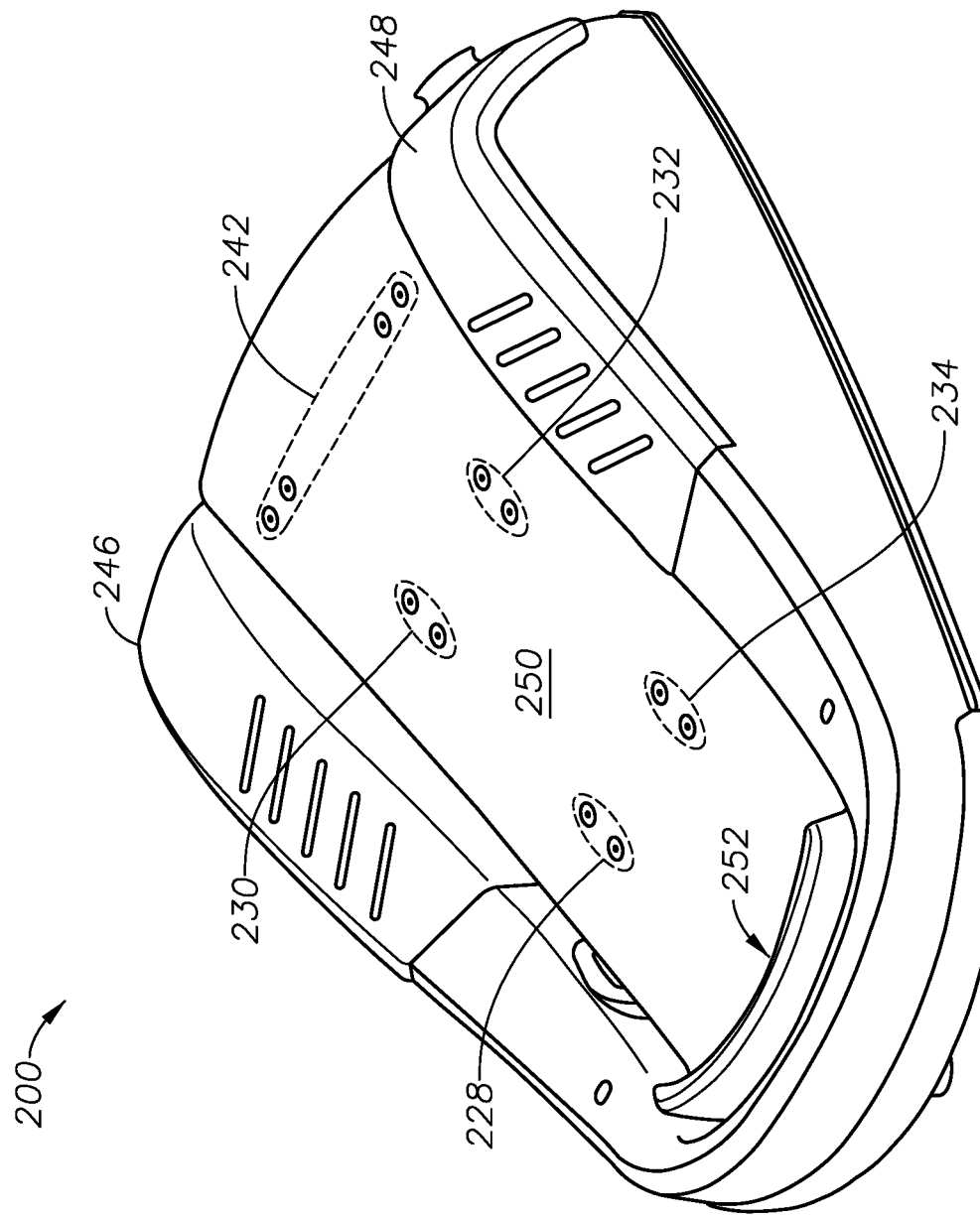

FIGS. 2A and 2B illustrate layered views of a treadle assembly of a foot controller 200 with a base 202, a frame 204, and with the treadle assembly having a treadle plate 210, an adjustable treadle surface member 250, and a latch 260 according to some embodiments of the present technology. FIG. 2A illustrates a layered view of the foot controller 200 exposing a treadle plate 210. The treadle plate 210 can be rotatably coupled with the base 202 of the foot controller at or near a proximal end 216 of the treadle plate 210. The treadle plate 210 can include one or more channels 220, 222 in the surface of the treadle plate 210 that extends in a direction from the proximal end 216 of the treadle plate 210 to the distal end 218 of the treadle plate 210. The channels 220, 222 can house one or more rails 224, 226 upon which one or more shuttles 228, 230, 232, 234 are slidably coupled. Also shown in FIG. 2A are a latch 260 mounted to the treadle plate 210 via a latching mount 242. A latching assembly that includes the latch 260 is described in greater detail below.

FIG. 2B illustrates a layered view of the foot controller 200 with the treadle plate 210 layered with an adjustable treadle surface member 250 coupled to the treadle plate 210 via the shuttles 228, 230, 232, 234 and the latching mount 242. Through the shuttles' 228, 230, 232, 234 slidable coupling with the rails 224, 226, the adjustable treadle surface member 250 can adjustably slide relative to the treadle plate 210.

The foot controller 200 can also include buttons 246, 248 at a distal end of the frame 204. In addition, the adjustable treadle surface member 250 includes a heel cup 252 at the proximal end of the adjustable treadle surface member 250. When an operator rests his foot against the heel cup 252, the position of the heel cup 252 impacts the placement of the operator's foot relative to the buttons 246, 248. Adjusting the adjustable treadle surface member 250 therefore accommodates a greater variety of operators because operators have various foot sizes.

Although the adjustable treadle surface member 250 is described as a "surface," those with ordinary skill in the art having the benefit of the disclosure will readily appreciate that the adjustable treadle surface member 250 is not necessarily the top surface and that other materials, films, paint, etc. can be applied, deposited, coupled, etc. to the adjustable treadle surface member 250 while maintaining the utility of the foot controller 200.

Figure 3:
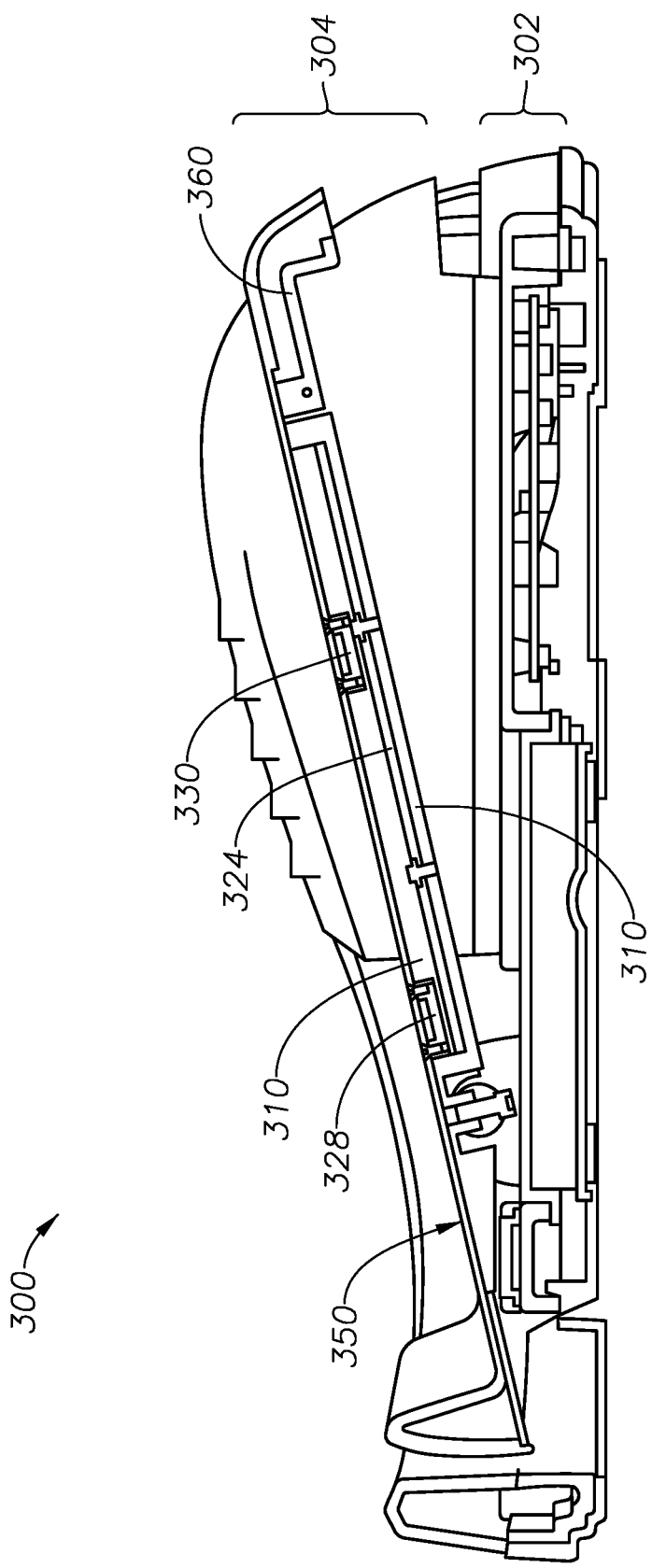
FIG. 3 illustrates a cut-away view of a foot controller with a treadle assembly having a treadle plate, an adjustable treadle surface member, and a latch according to some embodiments of the present technology.

FIG. 3 illustrates a cut-away view of a foot controller 300 with a base 302, a frame 304, and with the treadle assembly having a treadle plate 310, an adjustable treadle surface member 350, and a latch 360 according to some embodiments of the present technology. As shown, shuttles 328, 330 are slidably coupled to a rail 324 in channel (not labeled) in the surface of the treadle plate 310. The shuttles 328, 330 are also coupled to the adjustable treadle surface member 350 and the adjustable treadle surface member 350 can adjustably slide relative to the treadle plate 210.

In some cases, the foot controller 300 also includes a spring assembly (not shown) coupled to the base 302 and to the treadle assembly. The spring assembly can place the treadle assembly at the default angular position with respect to the base 302 and can be configured to compress with the application of torque on the treadle assembly by a downward rotational depression of the treadle assembly.

Figure 4:
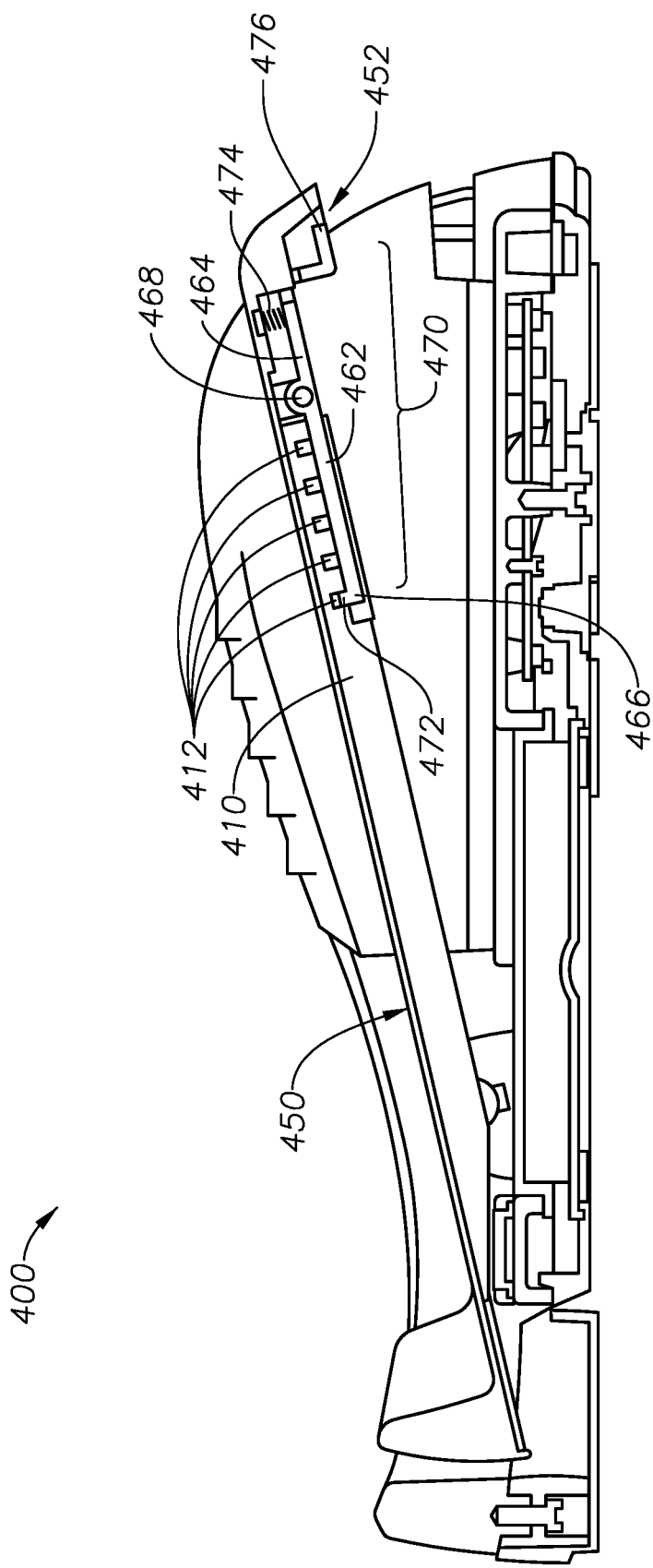
FIG. 4 illustrates a side view of a latching assembly used in a foot controller with an adjustable treadle.

FIG. 4 illustrates a side view of a latching assembly 470 used in a foot controller 400 with the treadle assembly having a treadle plate 410 and an adjustable treadle surface member 450 according to some embodiments of the present technology.

The latching assembly 470 includes a lever 462 with a lever distal end 464 arranged in a proximity to a distal end of the adjustable treadle surface member 450 and a lever proximal end 466 extending underneath the treadle plate 410 in a direction towards a proximal end of the treadle plate 410. The latching assembly 470 also includes a latch axis pin 468 coupled to the adjustable treadle surface member 450. The lever 462 is rotationally coupled with the latch axis pin 468 and the latch axis pin 468 can act as a fulcrum for the lever 462.

The treadle plate 410 includes a plurality of notches 412 on a bottom surface of the treadle plate 410 and substantially adjacent to the distal end of the treadle plate 410. In addition, the lever 462 includes a protrusion 472 at or near the lever proximal end 466. Actuation of the lever 462 about the latch axis pin 468 disengages the protrusion 472 from a first notch 412 on a bottom surface of the treadle plate 410 allowing the adjustable treadle surface member 450 to slide, e.g. on shuttles (not shown) along rails (not shown). The protrusion 472 can selectively engage the first notch 412 or another of the notches 412 on a bottom surface of the treadle plate 410 to adjust the adjustable treadle surface member 450 relative to the treadle plate. In some cases, the lever 462 includes a plurality of protrusions that selectively engage a plurality of the notches 412.

In some other embodiments, the engagement of the treadle plate 410 with the adjustable treadle surface member 450 is achieved by friction.

The latching assembly 470 can also include a latch spring 474 located near the lever distal end 464 between the lever 462 and the adjustable treadle surface member 450. The latch spring 474 provides resistance to a movement of the lever 462 about the latch axis pin 468 fulcrum. The latch spring 474 also provides a return force on the lever 462 after removal of the actuation force. In some other cases, the latch spring can be a torsion spring.

In some cases, the adjustable treadle surface member 450 further extends downward at the distal end of the adjustable treadle surface member 450 to shield the latch assembly 470 and can terminate in an opening 452. The latch assembly 470 can also include a latch button 476 located at the lever distal end 464 and extending downward to be substantially positioned in the opening 452. The latch button 476 can be used to provide the actuation force on the lever 462.

Although a specific latching assembly 470 is described explicitly herein, those with ordinary skill in the art having the benefit of the disclosure will readily appreciate that other latching assemblies can be used while maintaining the utility of the foot controller 400. For example, the latching function could be accomplished using a linearly spring-loaded plunger pin, a latch could oriented at a right angle with intermediate linkage (rotational or sliding) that converts the motion from lengthwise to normal, etc.

Figure 5A:
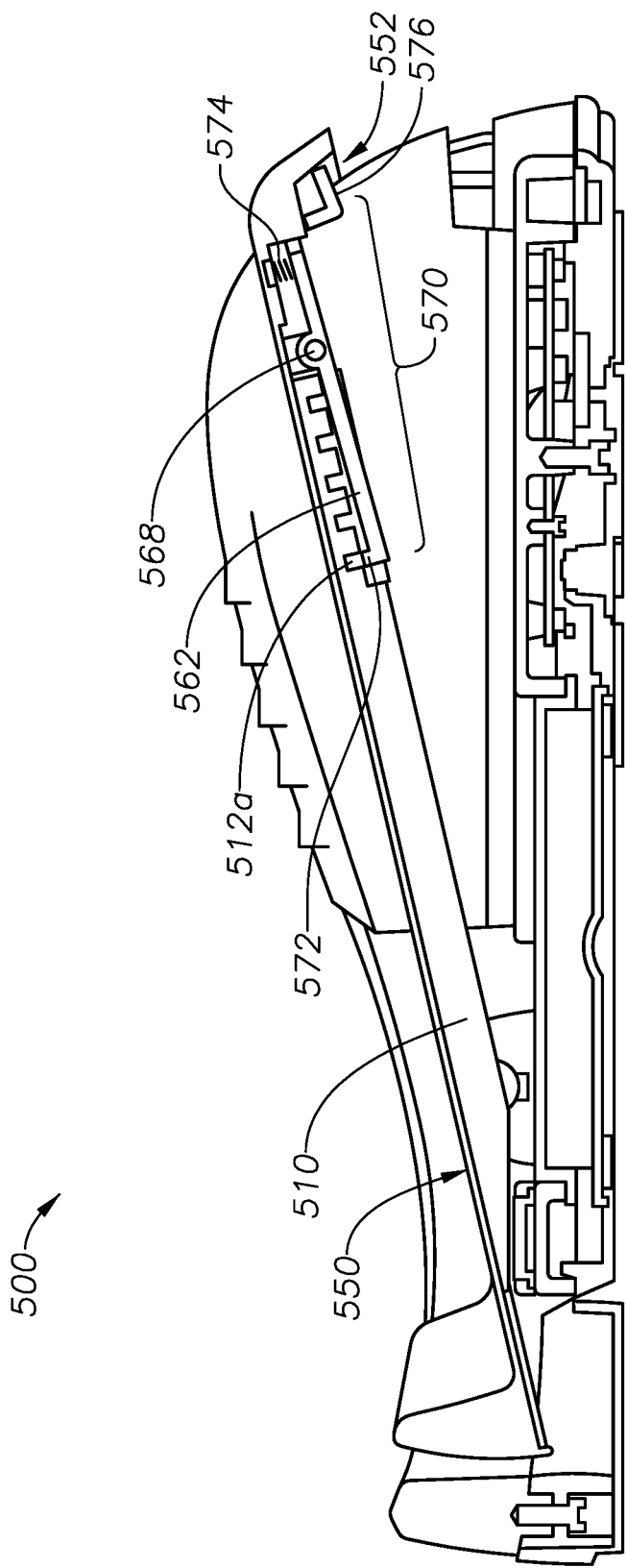
FIGS. 5A and 5B illustrate side views of a foot controller with an adjustable treadle surface member adjustably coupled with a treadle plate and latching assembly according to some embodiments of the present technology.
Figure 5B:
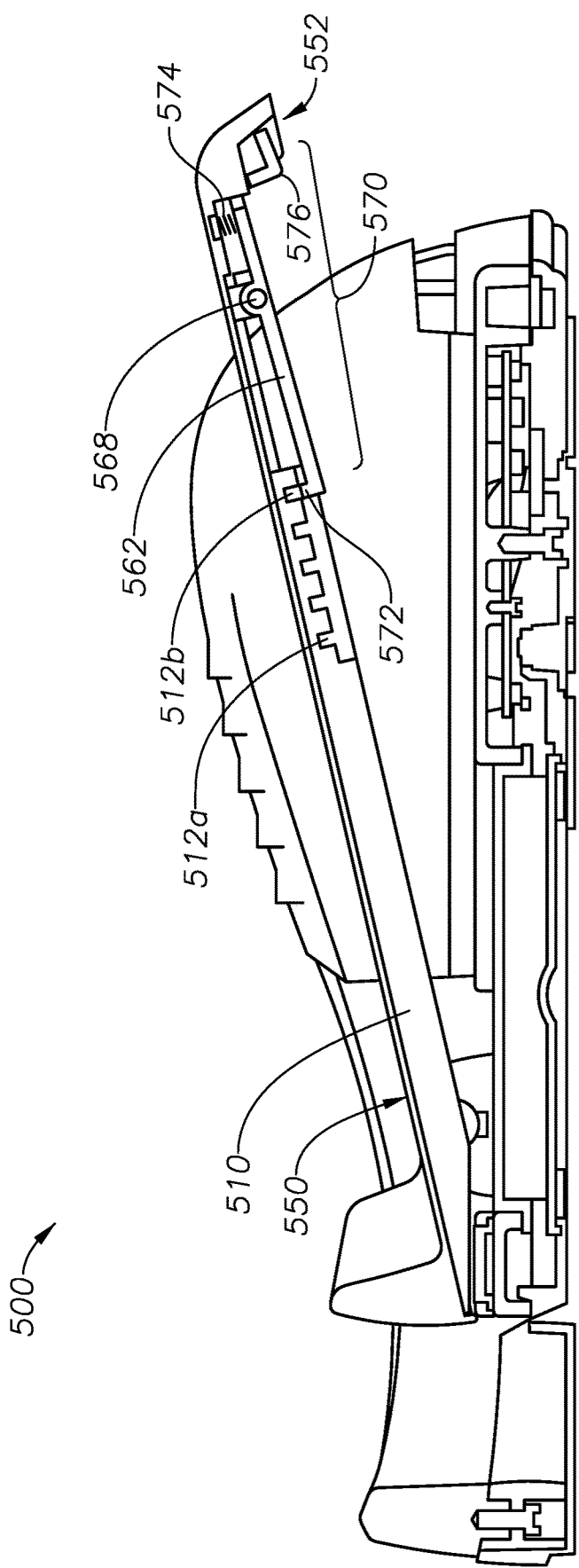

FIGS. 5A and 5B illustrate side views of a foot controller 500 with an adjustable treadle surface member 550 adjustably coupled with a treadle plate 510 and latching assembly 570 according to some embodiments of the present technology.

As shown in FIG. 5A, a latch button 576 positioned in the opening 552 of the adjustable treadle surface member 550 has been actuated causing the lever 562 to rotate about the latch axis pin 568. As an effect of the rotation, the protrusion 572 at the proximal end of the lever 562 becomes disengaged from a first notch 512a and the adjustable treadle surface member 550 is free to slide on the treadle plate 510 via shuttles (not shown) on the rails (not shown) in the treadle plate 510.

As shown in FIG. 5B, the adjustable treadle surface member 550 has been slid towards the distal end of the foot controller 500 and the protrusion 572 at the proximal end of the lever 562 is positioned beneath a second notch 512b. After the removal of the actuation force on the latch button 576, the latch spring 574 provides a returning force on the proximal end of the lever 562 to engage the protrusion 572 with the second notch 512b and secure the adjustable treadle surface member 550 in place.

Figure 6:
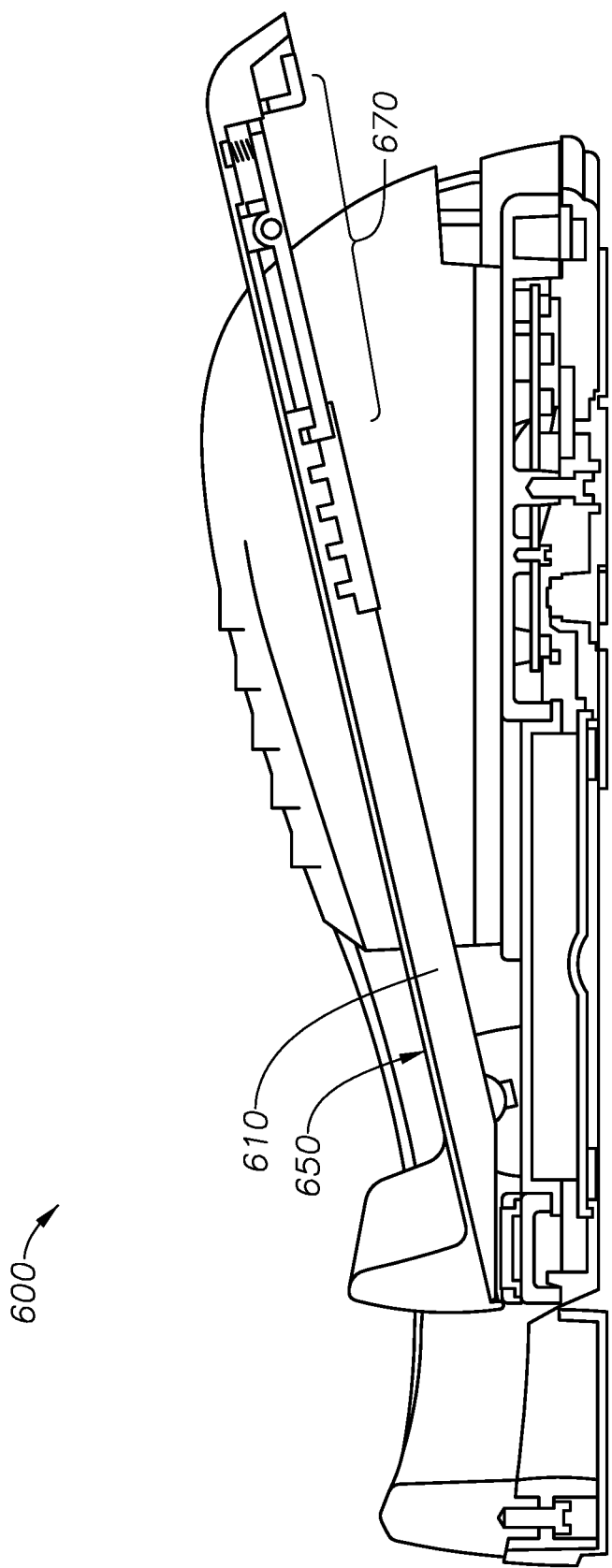
FIG. 6 illustrates a side view of a foot controller with an adjustable treadle surface member adjusted at a fixed position relative to a treadle plate.

FIG. 6 illustrates a side view of a foot controller 600 with an adjustable treadle surface member 650 adjusted to a distal position on the treadle plate 610 with the latching assembly 670 securing the adjustable treadle surface member 650 in place.

Figure 7A:
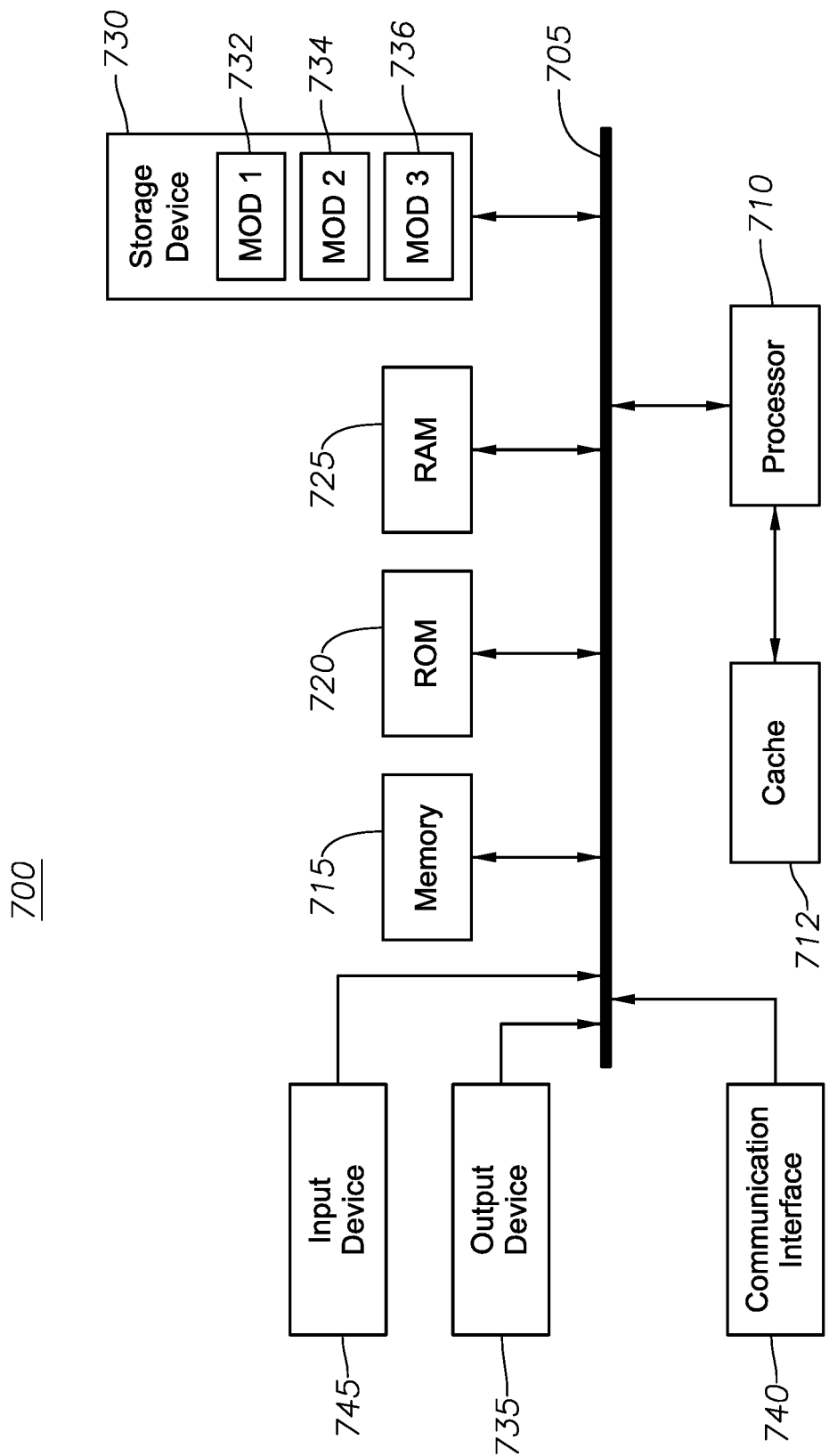
FIGS. 7A and 7B illustrate possible system embodiments.

FIG. 7A illustrates a conventional system bus computing system architecture 700 wherein the components of the system are in electrical communication with each other using a bus 705. Exemplary system 700 includes a processing unit (CPU or processor) 710 and a system bus 705 that couples various system components including the system memory 715, such as read only memory (ROM) 720 and random access memory (RAM) 725, to the processor 710. The system 700 can include a cache of high-speed memory connected directly with, in close proximity to, or integrated as part of the processor 710. The system 700 can copy data from the memory 715 and/or the storage device 730 to the cache 712 for quick access by the processor 710. In this way, the cache can provide a performance boost that avoids processor 710 delays while waiting for data. These and other modules can control or be configured to control the processor 710 to perform various actions. Other system memory 715 may be available for use as well. The memory 715 can include multiple different types of memory with different performance characteristics. The processor 710 can include any general purpose processor and a hardware module or software module, such as module 1 732, module 2 734, and module 3 736 stored in storage device 730, configured to control the processor 710 as well as a special-purpose processor where software instructions are incorporated into the actual processor design. The processor 710 may essentially be a completely self-contained computing system, containing multiple cores or processors, a bus, memory controller, cache, etc. A multi-core processor may be symmetric or asymmetric.

To enable user interaction with the computing device 700, an input device 745 can represent any number of input mechanisms, such as a microphone for speech, a touch-sensitive screen for gesture or graphical input, keyboard, mouse, motion input, speech and so forth. An output device 735 can also be one or more of a number of output mechanisms known to those of skill in the art. In some instances, multimodal systems can enable a user to provide multiple types of input to communicate with the computing device 700. The communications interface 740 can generally govern and manage the user input and system output. There is no restriction on operating on any particular hardware arrangement and therefore the basic features here may easily be substituted for improved hardware or firmware arrangements as they are developed.

Storage device 730 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 725, read only memory (ROM) 720, and hybrids thereof.

The storage device 730 can include software modules 732, 734, 736 for controlling the processor 710. Other hardware or software modules are contemplated. The storage device 730 can be connected to the system bus 705. In one aspect, a hardware module that performs a particular function can include the software component stored in a computer-readable medium in connection with the necessary hardware components, such as the processor 710, bus 705, display 735, and so forth, to carry out the function.

Figure 7B:
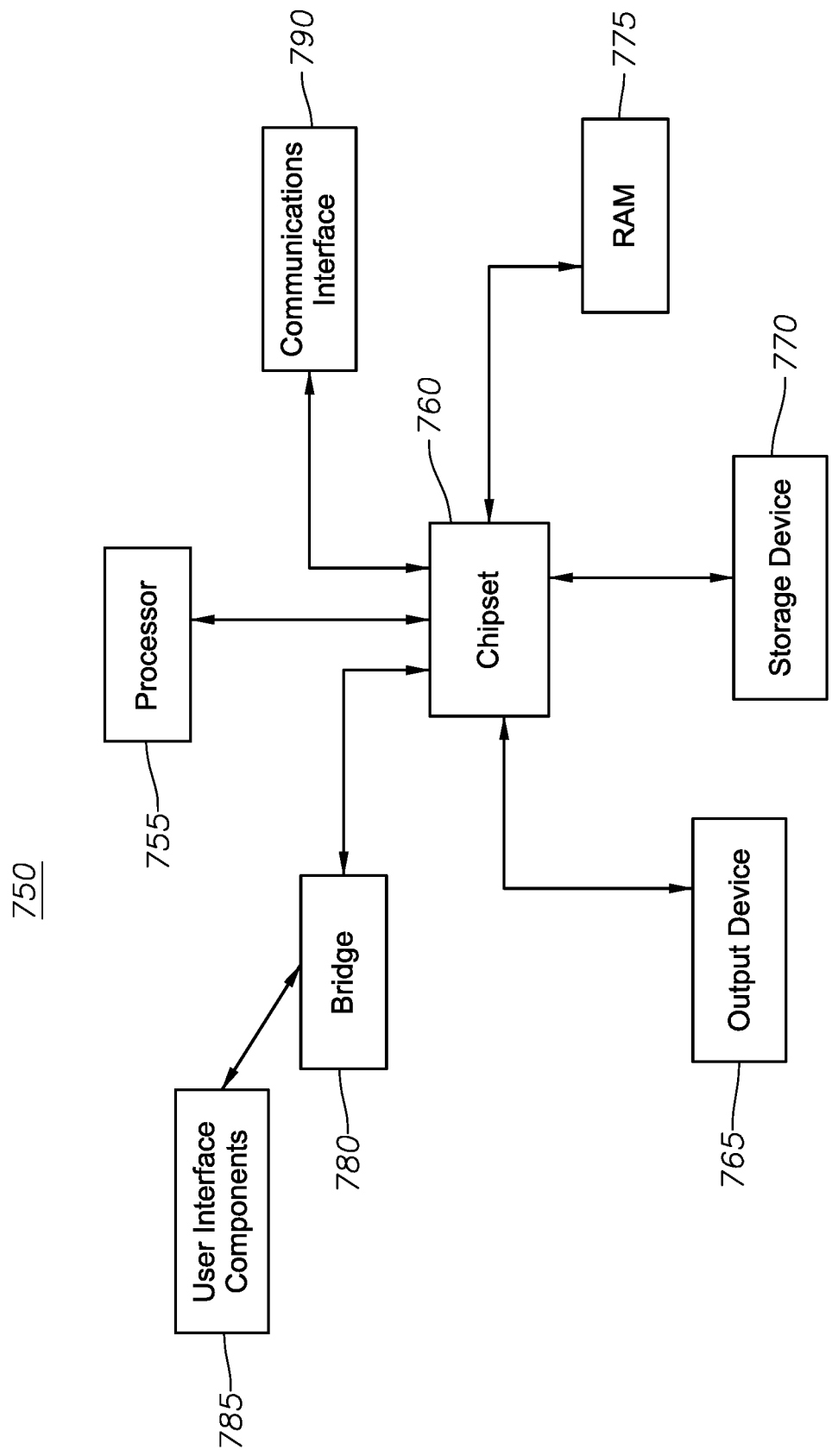

FIG. 7B illustrates a computer system 750 having a chipset architecture that can be used in executing the described method and generating and displaying a graphical user interface (GUI). Computer system 750 is an example of computer hardware, software, and firmware that can be used to implement the disclosed technology. System 750 can include a processor 755, representative of any number of physically and/or logically distinct resources capable of executing software, firmware, and hardware configured to perform identified computations. Processor 755 can communicate with a chipset 760 that can control input to and output from processor 755. In this example, chipset 760 outputs information to output 765, such as a display, and can read and write information to storage device 770, which can include magnetic media, and solid state media, for example. Chipset 760 can also read data from and write data to RAM 775. A bridge 780 for interfacing with a variety of user interface components 785 can be provided for interfacing with chipset 760. Such user interface components 785 can include a keyboard, a microphone, touch detection and processing circuitry, a pointing device, such as a mouse, and so on. In general, inputs to system 750 can come from any of a variety of sources, machine generated and/or human generated.

Chipset 760 can also interface with one or more communication interfaces 790 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 755 analyzing data stored in storage 770 or 775. Further, the machine can receive inputs from a user via user interface components 785 and execute appropriate functions, such as browsing functions by interpreting these inputs using processor 755.

It can be appreciated that exemplary systems 700 and 750 can have more than one processor 710 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A foot controller comprising:
   a base;
   a treadle assembly comprising:
      a treadle plate rotatably coupled with the base at a proximal end of the treadle plate and having a variable angular position with respect to the base at a distal end of the treadle plate, the treadle plate further comprising:
         at least one channel in a surface of the treadle plate that extends in a direction from the proximal end of the treadle plate to the distal end of the treadle plate;
         at least one rail in the at least one channel;
         at least one shuttle slidably coupled to the at least one rail; and
         a plurality of notches on a bottom surface of the treadle plate and substantially adjacent to the distal end of the treadle plate;
      an adjustable treadle surface member coupled to the treadle plate via the at least one shuttle; and
      a latch assembly including a lever with a lever distal end arranged in a proximity to a distal end of the adjustable treadle surface member and a lever proximal end extending underneath the treadle plate in a direction towards a proximal end of the treadle plate, wherein the lever proximal end includes at least one protrusion that selectively engages with at least one of the plurality of notches on a bottom surface of the treadle plate, thereby sliding the at least one shuttle on the at least one rail, and thereby adjusting the adjustable treadle surface member relative to the treadle plate.

2. The foot controller of claim 1, wherein the treadle plate further comprises two channels in the surface of the treadle plate that extends in a direction from the proximal end of the treadle plate to the distal end of the treadle plate, and wherein each of the two channels includes one rail.

3. The foot controller of claim 2, wherein the treadle plate further comprises two shuttles slidably coupled to each of the rails in the two channels.

4. The foot controller of claim 1, wherein the latch assembly further comprises:
   a latch axis pin that acts as a fulcrum to selectively engage the at least one protrusion with at least one of the plurality of notches on a bottom surface of the treadle plate.

5. The foot controller of claim 4, wherein the adjustable treadle surface member is substantially planar from a heel cup at a proximal end of the adjustable treadle surface member to the distal end of the adjustable treadle surface member.

6. The foot controller of claim 5, wherein the adjustable treadle surface member further extends downward at the distal end of the adjustable treadle surface member to shield the latch assembly and terminates in an opening.

7. The foot controller of claim 6, wherein the latch assembly further comprises:
   a latch button located at the distal end of the lever and extending downward to be substantially positioned in the opening.

8. The foot controller of claim 4, wherein the latch axis pin separates the lever distal end and the lever proximal end.

9. The foot controller of claim 8, wherein the latch assembly further comprises:
   a latch spring located substantially adjacent to the lever distal end between the lever and the adjustable treadle surface member, wherein the latch spring provides resistance to a movement of the lever about the fulcrum and a return force on the lever.

10. The foot controller of claim 1, further comprising a heel cup at a proximal end of the adjustable treadle surface member.

11. The foot controller of claim 1, wherein the adjustable treadle surface member comprises a substantially flat surface substantially sized to accommodate an operator's foot.

12. The foot controller of claim 1, further comprising:
a control assembly configured to determine an angular position of the treadle assembly relative to the base and to convert the angular position into a first signal describing the angular position of the treadle assembly.

13. The foot controller of claim 1, wherein the lever includes a plurality of protrusions that selectively engage with one of the plurality of notches on the bottom surface of the treadle plate.

14. The foot controller of claim 1, wherein the foot controller is communicatively coupled with a surgical console, and wherein the first signal describing the angular position of the pedal surface is used to control a surgical tool coupled with the surgical console.

15. The foot controller of claim 1, further comprising:
a spring assembly coupled to the base and to the treadle assembly, the spring assembly configured to place the treadle assembly at a default angular position with respect to the base and configured to compress with an application of torque on the treadle assembly by a downward rotational depression of the treadle assembly.

* * * * *